(12) United States Patent
Nishimori

(10) Patent No.: US 11,366,126 B2
(45) Date of Patent: Jun. 21, 2022

(54) ANALYSIS APPARATUS

(71) Applicant: HORIBA, Ltd., Kyoto (JP)

(72) Inventor: Masashi Nishimori, Kyoto (JP)

(73) Assignee: HORIBA, Ltd., Kyoto (JP)

( * ) Notice: Subject to any disclaimer, the term of this patent is extended or adjusted under 35 U.S.C. 154(b) by 376 days.

(21) Appl. No.: 16/034,726

(22) Filed: Jul. 13, 2018

(65) Prior Publication Data

US 2019/0018028 A1 Jan. 17, 2019

(30) Foreign Application Priority Data

Jul. 14, 2017 (JP) .............................. JP2017-138408

(51) Int. Cl.
 *G01N 35/00* (2006.01)
 *B05B 15/50* (2018.01)
 (Continued)

(52) U.S. Cl.
 CPC ....... *G01N 35/00584* (2013.01); *B05B 15/50* (2018.02); *G01N 35/0092* (2013.01);
 (Continued)

(58) Field of Classification Search
 None
 See application file for complete search history.

(56) References Cited

U.S. PATENT DOCUMENTS

| 4,817,443 A | * | 4/1989 | Champseix | ........ G01N 35/1004 |
| | | | | 73/864.22 |
| 2001/0010936 A1 | * | 8/2001 | Richards | ............ G01N 35/1002 |
| | | | | 436/49 |

(Continued)

FOREIGN PATENT DOCUMENTS

| EP | 2804005 A1 | 11/2014 |
| EP | 3032264 A1 | 6/2016 |

(Continued)

OTHER PUBLICATIONS

European Patent Office, Extended European Search Report Issued in Application No. 18183291.6, dated Dec. 20, 2018, Germany, 8 pages.

(Continued)

*Primary Examiner* — Benjamin R Whatley
*Assistant Examiner* — Curtis A Thompson
(74) *Attorney, Agent, or Firm* — Alleman Hall Creasman & Tuttle LLP

(57) ABSTRACT

Provided is an analysis apparatus having a control part having a preparatory action setting part for determination of whether the first and second controls are performed or the third and fourth controls are performed. The first control sets a sleep-planned part to a sleep state at a first time point when the state of non-use of the analysis apparatus has lasted for a predetermined time length, and then causes performance of a preparatory action by a first predetermined part; the second control resumes the operation of the analysis apparatus when a command signal to resume the operation is received; the third control places a sleep-planned part in a sleep state at a second time point when the state of non-use has lasted for a time length; and the fourth control causes a preparatory action of a second predetermined part to resume operation.

4 Claims, 4 Drawing Sheets

(51) Int. Cl.
  G05B 15/02 (2006.01)
  G01N 35/10 (2006.01)
  *G01N 33/49* (2006.01)
  *G01N 33/53* (2006.01)

(52) U.S. Cl.
  CPC ......... *G01N 35/1004* (2013.01); *G05B 15/02* (2013.01); *G01N 33/49* (2013.01); *G01N 33/491* (2013.01); *G01N 33/53* (2013.01); *G01N 33/5304* (2013.01); *G01N 35/00* (2013.01); *G01N 35/00871* (2013.01); *G01N 2035/0091* (2013.01); *G01N 2035/0094* (2013.01); *G01N 2035/00891* (2013.01); *G01N 2333/46* (2013.01)

(56) References Cited

U.S. PATENT DOCUMENTS

| | | | | |
|---|---|---|---|---|
| 2003/0070498 | A1* | 4/2003 | Ohyama | G01N 35/1079 73/863.01 |
| 2008/0187951 | A1* | 8/2008 | Nagai | G01N 33/5094 435/29 |
| 2008/0302393 | A1 | 12/2008 | Jafari et al. | |
| 2009/0035182 | A1* | 2/2009 | Soma | G01N 35/00693 422/82.05 |
| 2011/0000763 | A1* | 1/2011 | Kimura | G01N 35/04 198/340 |
| 2012/0251391 | A1* | 10/2012 | Hagiwara | G01N 35/00584 422/68.1 |
| 2012/0275956 | A1* | 11/2012 | Wakamiya | G01N 35/00663 422/68.1 |
| 2013/0235777 | A1* | 9/2013 | Takaki | H04W 52/0251 370/311 |
| 2013/0311243 | A1* | 11/2013 | Taki | G01N 35/0092 705/7.38 |
| 2014/0341779 | A1* | 11/2014 | Takemoto | G01N 35/04 422/73 |
| 2016/0154016 | A1* | 6/2016 | Yamashita | G01N 35/00871 436/50 |
| 2017/0146500 | A1* | 5/2017 | Kanazawa | G01N 30/88 |
| 2018/0246132 | A1* | 8/2018 | Mori | G01N 35/1002 |

FOREIGN PATENT DOCUMENTS

| | | | | |
|---|---|---|---|---|
| JP | | S63139256 A | 6/1988 | |
| JP | | 2005241612 A | 9/2005 | |
| JP | | 2011179825 A | 9/2011 | |
| JP | | 2014224754 A | 12/2014 | |
| WO | WO-2015198389 A1 * | | 12/2015 | ............. G01N 35/00 |

OTHER PUBLICATIONS

Japan Patent Office, Decision to Grant a Patent in Application No. 2017-138408, dated Mar. 30, 2021, 6 pages.

* cited by examiner

ANALYSIS APPARATUS

FIELD OF THE INVENTION

The present invention relates to an analysis apparatus for analyzing specimen.

BACKGROUND OF THE INVENTION

Analyzer that performs analysis (including particle counting) of specimens such as blood, urine and the like is generally constituted of a measuring part for performing specimen measurements and a control part for controlling the action of the measuring part. The measuring part includes devices relating to the measurement such as a driving part having a sampling nozzle and a driving unit for driving the sampling nozzle, a measuring chamber, various pumps and the like. For example, in hematological analysis (including blood cell counting), a sampling nozzle sucks a given amount of blood contained in a specimen container, dispenses same to one or more measuring chambers, and the measurement is performed in the measuring chamber. In addition to control of the action of the measuring part, the control unit also analyzes a detection signal obtained from the measuring part (e.g., patent document 1 and the like).

For the purpose of energy saving, some of the conventional analysis apparatuses are configured to automatically enter a sleep state when they are not used for a predetermined period of time (e.g., patent document 2 and the like). In the sleep state, for example, electric power supply to the measuring part is stopped, and the control part waits for the input or reception of the command signal for resuming the analysis.

Patent Document 1 JP-A-2014-224754
Patent Document 2 JP-A-2005-241612

Conventionally, the analysis apparatus is configured to perform necessary preparatory action such as blank measurement in which measurement is performed without a specimen, filling of a buffer tank (dilution liquid reservoir tank) with a dilution liquid, wetting of a sampling nozzle with a dilution liquid and the like when returning from the sleep state to the analyzable state. Conventionally, therefore, when the user wishes to resume the analysis by the analysis apparatus after the apparatus enters the sleep state, the user has to wait until the aforementioned preparatory action is completed, thus posing a problem that analysis cannot be performed even when it is desired immediately.

SUMMARY OF THE INVENTION

The purpose of the present invention is to solve the above-mentioned problem and provide an analysis apparatus having a function to enter a sleep state and capable of resuming operation more rapidly from the sleep state.

The main constitution of the present invention to solve the above-mentioned problem is as follows.

[1] An analysis apparatus comprising a measuring part for performing measurement for the analysis of a specimen, and a control part for controlling the measuring part and analyzing a detection signal from the measuring part,
wherein
the control part is provided with a preparatory action setting part that receives a setting of a user as to whether the control part performs the following first and second controls or the following third control and fourth controls, and is constituted to perform the first and second controls, or the third and fourth controls according to the setting of the preparatory action setting part, the first control sets a sleep-planned part for the first control of the analysis apparatus to a sleep state at a time point t1 when the state of non-use of the analysis apparatus has lasted for a predetermined time length T1, and causes, after the time point t1, performance of a preparatory action for operation resumption by a predetermined part for the first control requiring a preparatory action, the second control resumes the operation of the analysis apparatus when the control part receives a command signal to resume the operation after the first control, the third control places a sleep-planned part for the third control of the analysis apparatus in a sleep state at a time point t10 when the state of non-use of the analysis apparatus has lasted for a predetermined time length T10, and the fourth control causes, when a command signal to resume the operation is received after the third control, a preparatory action of a predetermined part for the fourth control requiring a preparatory action to resume operation, and then resumes the operation of the analysis apparatus.

[2] The analysis apparatus according to [1], wherein
the measuring part comprises a sampling nozzle driving part comprising a sampling nozzle, a cleaning device and a driving unit for moving them, the sampling nozzle is constituted to move in the horizontal direction together with a cleaning device while being inserted in a through-hole provided in the vertical direction in the cleaning device, and move in the vertical direction relative to the cleaning device, the cleaning device comprises a liquid supply port on a lower side part of the through-hole for supplying a liquid on the outer surface of the sampling nozzle, an O-ring groove is provided in an inner wall surface of the through-hole, an O-ring is set on the O-ring groove, and the O-ring seals the clearance between the through-hole and the sampling nozzle while allowing the sampling nozzle to move in the vertical direction, and in the preparatory action, the liquid is supplied on the outer surface of the sampling nozzle by the cleaning device, the sampling nozzle reciprocates in the vertical direction by the driving unit, whereby the liquid is supplied as a lubricating liquid to a contact interface between the O-ring and the sampling nozzle.

[3] The analysis apparatus according to [1] or [2], wherein
the preparatory action includes a blank measurement in a predetermined measuring chamber, when the control part is set by the preparatory action setting part to execute the first control and the second control, the blank measurement is performed in the preparatory action without injecting or discharging the liquid into or from the predetermined measuring chamber, and when the control part is set by the preparatory action setting part to not execute the first control and the second control, the blank measurement is performed after injecting and discharging the liquid into and from the predetermined measuring chamber in the preparatory action.

[4] The analysis apparatus according to any of [1]-[3], wherein
the preparatory action includes a blank measurement in the measuring chamber, and
the control part stores results of data analysis of the blank measurement.

The analysis apparatus according to the present invention is constituted to set a predetermined sleep-planned part in the analysis apparatus in a sleep state and other predetermined parts to perform a preparatory action to resume the analysis. With this constitution, when the operation is resumed within a predetermined time after performing the preparatory action, the operation can be resumed omitting the preparation action. Therefore, it is possible to resume analysis faster from the sleep state. Also, the analysis apparatus according to the present invention is provided with a preparatory action setting part. The preparatory action setting part makes it possible for the user to set a part to enter the sleep state similar to the conventional state without performing the preparatory action. By providing the preparatory action setting part, the user can select whether to put a part in a sleep state that can resume operation quickly or in a sleep state that can save energy and materials more.

BRIEF DESCRIPTION OF THE DRAWINGS

FIG. 4(a) is a top view of the sampling nozzle and the cleaning device, and FIG. 4(b) is a X-X sectional view of FIG. 4(a).

Figure 1:
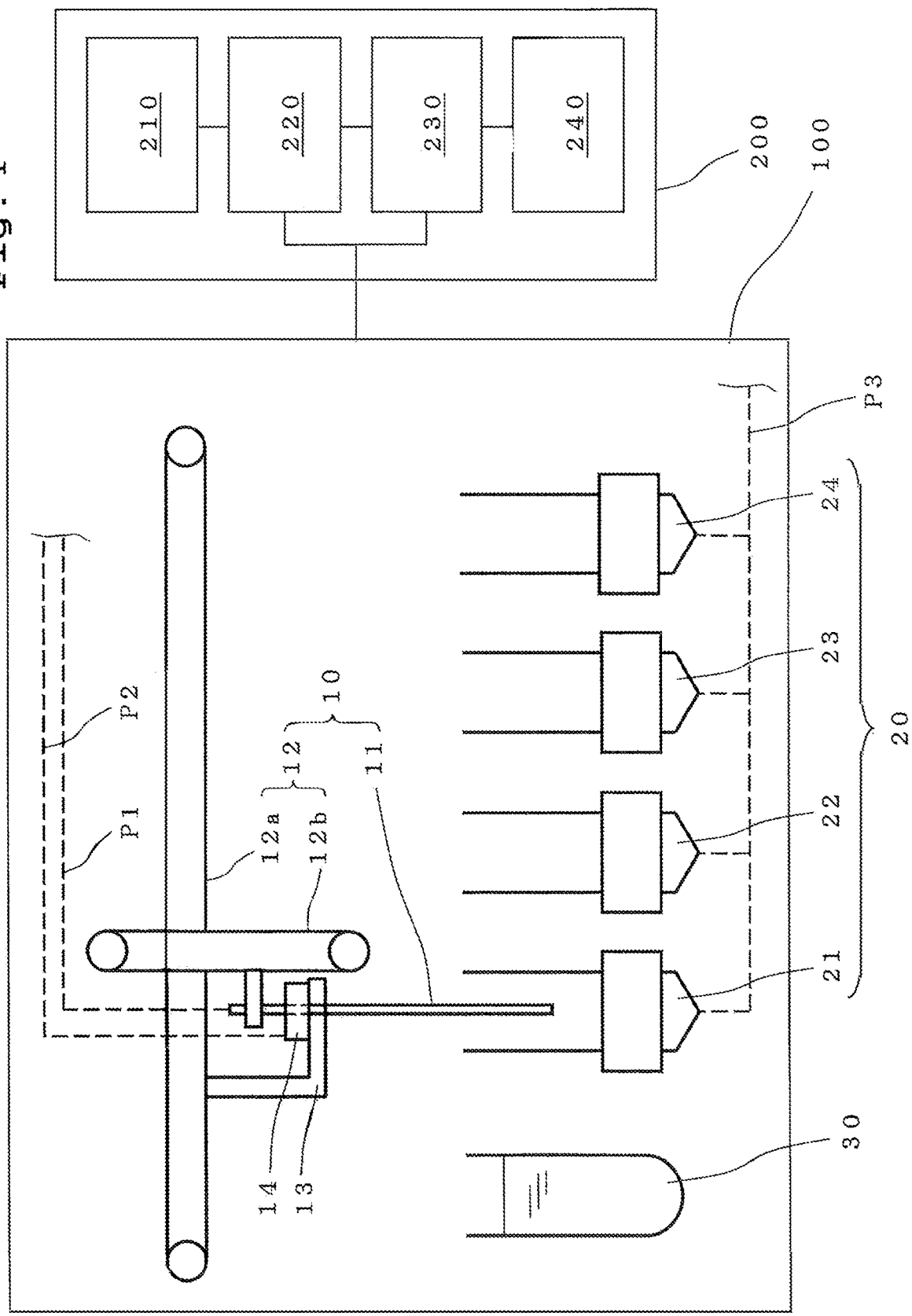
FIG. 1 is a block diagram showing one embodiment of the constitution of the analysis apparatus according to the present invention. In this Figure, the relationship between the structural parts involved in the measurement such as device, mechanism, piping and the like and the control part is shown with a block, and the electrical wiring is not shown.

The reference characters in the Figures show the following. 10; sampling nozzle driving part, 11; sampling nozzle, 12; driving unit, 20; measuring chamber, 30; specimen container, 100; measuring part, 200; control part, 210; preparatory action setting part.

DETAILED DESCRIPTION OF THE INVENTION

The analysis apparatus according to the present invention (sometimes to be also referred to as the apparatus) is explained in detail below by illustrating examples.

FIG. 1 shows one embodiment of the main parts of the apparatus. As shown in FIG. 1, the apparatus 1 comprises at least a measuring part 100 and a control part 200. FIG. 1 is a block diagram showing the relationship between the measuring part 100 and the control part 200 and concrete electrical wiring is not shown. In the example of FIG. 1, the apparatus is a blood analysis apparatus for counting of blood cells and classifying of white blood cells, and the measuring part 100 includes a sampling nozzle driving part 10, measuring chamber 20, piping P1, P2, P3 and the like. The piping also includes various pumps, electromagnetic valve device, liquid cleaning agent tank and dilution liquid tank (these are not shown). In addition, a specimen container 30 is set on the apparatus. The control part 200 is a control device constituted to control the action and state of each part of the measuring part 100, analyze detection signals sent from the measuring part 100 and output the analysis results. In the following, the explanation of the action of the measuring part is also the explanation on the control of the control part that makes the measuring part act as indicated.

In the present invention, the control part 200 is constituted to perform either one of the first control and the second control, and either one of the third control and the fourth control according to the setting by the user. That is, the control part 200 is constituted to be able to handle both the first and second controls, and the third and fourth controls, so that it can always perform irrespective of the selection.

When the first control and the second control are selected, a preparatory action is performed in the first control so that the aforementioned preparatory action can be omitted in resuming the operation from the sleep state in the second control and analysis can be resumed more rapidly from the sleep state. On the other hand, when the third control and the fourth control are selected, a time for the preparatory action is necessary in resuming the operation; however, a sleep state with more energy and material savings is achieved.

The control part and the control thereof are now explained.

[Control Part]

The control part is constituted to control the action of each part of the measuring part (action of sampling nozzle driving part, measurement action in each measuring chamber and the like), process (calculate) the detection signals sent from the measuring part for analysis, and output the analysis results. In the example of FIG. 1, the control part 200 has an action control part 220 that controls the action of each part of the measuring part 100, a data processing part 230 that processes the detection signal and outputs the analysis results, and a storage part 240 that stores the data processing results and the like. The preparatory action setting part 210 is described below. The control part 200 preferably also has the function to not only process for action control or analysis, but also store and manage processed data, analysis results, state of each part and the like. The control part may be constructed by a logic circuit and the like. However, a computer is appropriate and the control part may include an external computing device, various driving devices (sensor, driver for motor and the like), external storage device and various interfaces. In the following, the contents of control are explained assuming that the control part is mainly constituted of a computer.

[Preparatory Action Setting Part]

In the present invention, a preparation action setting part 210 is provided in the control part as a part for accepting the setting by the user as to whether the control part performs the first and second controls or the third and fourth controls. In the following, the setting by the preparatory action setting part is also called "preparatory action setting", the setting for performing the first and second controls is also called "preparatory action setting ON", and the setting for performing the third and fourth controls is also called "preparatory action setting OFF".

With preparatory action setting ON, when the state in which the apparatus is not used lasts for a predetermined time length T1 or T2, the above-mentioned preparatory action is always performed. Thus, materials such as liquid (dilution liquid) and the like and electric power are consumed compared to the preparatory action setting OFF. Thus, with preparatory action setting, the user can select immediate operation resumption by preparatory action setting ON (materials such as liquid and the like and electric power are consumed more) or regular or normal operation resumption by preparatory action setting OFF (consumption of materials such as liquid and the like and electric power occurs only when resuming operation from the sleep state).

The preparatory action setting part 210 may have a physical switch to change preparatory action setting ON and preparatory action setting OFF, or may have a constitution in which preparatory action setting ON and preparatory action setting OFF are displayed on a display screen and the user inputs either on the screen.

[The First Control]

the first control sets, as shown in the time chart of FIG. 2, a sleep-planned part for the first control of the analysis apparatus (hereinafter to be also called "sleep-planned part (I)") to a sleep state at a time point t1 when the state of non-use of the analysis apparatus has lasted for a predetermined time length T1 from a time point when the apparatus was used the last time, and causes, at a time point simultaneously with or later than the time point t1, performance of a preparatory action for operation resumption by a predetermined part for the first control (hereinafter to be also called "predetermined part (I)") requiring the preparatory action. The sleep-planned part (I) is described later. The time point t1 may be a time point when the control part sends a command signal of a sleep state to the sleep-planned part (I). A time lag may be present between the time point t1 and the time point when the sleep-planned part (I) went into a sleep state.

The time point of putting the sleep-planned part (I) in a sleep state and the time point of the preparatory action of the predetermined part (I) may be the same or a time lag may be present between them. For example, when the control part is constituted to check the presence or absence of an input signal from each sensor or start switch at a regular time interval $\Delta T$, a time lag of maximum $\Delta T$ may occur from the aforementioned time point t1 to the time point when the absence of the command signal is determined. $\Delta T$ is not particularly limited, and may be not more than one second, a few seconds, a few minutes or several dozen minutes. When a command signal for resuming operation is received from the user during such time lag $\Delta T$, the control part may resume the operation of the apparatus immediately without causing the preparatory action.

In the first control, the predetermined part (I) selected to perform a preparatory action may be prepared for the command signal for resuming operation without stopping electric power supply after completion of the preparatory action. It is preferably put in a sleep state.

(Time Length T1)

The time length T1 is a length of the time of an unused state for placing the sleep-planned part (I) of the apparatus in the sleep state. The time length T1 is previously set. The time length T1 is not particularly limited, and may be determined according to the use state by the user. In the present invention, the predetermined part (I) performs the above-mentioned preparatory action when the time length T1 has elapsed. When a biological specimen such as blood or the like is the analysis target, the time length T1 is preferably about 90 min-120 min, particularly preferably 120 min. The time length T1 of about 90 min-120 min is preferable because the sampling nozzle is less likely to dry by the above-mentioned preparatory action. When the sampling nozzle is dry, O-ring 14*d* set in the below-mentioned cleaning device shown in FIGS. 4(*a*) and 4(*b*) may be worn away due to the friction of the O-ring 14*d* and the sampling nozzle.

When the time length T1 is shorter than 90 min, the above-mentioned preparatory action is performed uselessly and when the time length T1 is longer than 120 min, the sampling nozzle is highly likely dried undesirably.

A recommended time length T1 (e.g., 120 min and the like) may be set in the control part as an initial setting value. The control part may have a T1 setting part allowing the user to set a desired time length T1. The T1 setting part may have a constitution allowing the user to select from plural preset values or input time length T1.

(Sleep State)

In the sleep state, for example, the control part is maintained in a state in which it can start up after receiving an instruction signal for resuming operation (that is, a state waiting for input or reception of a command signal for resuming operation). The sleep state of the control part may be similar to standby (sleep) or hibernating state in the operation of computer. The control part (excluding display screen or indication lamp) may stay in an operation state without turning to a sleep state.

In the sleep state, supply of an electric power to an electric power consuming part to be in the sleep state is stopped.

The part to be in the sleep state includes sleep-planned part (I), a part to be in a sleep state after a preparatory action of the predetermined part (I), a part to be in a sleep state by the below-mentioned third control. The part to be in the sleep state includes, for example, the control part, various mechanism parts and electric or electronic part of the apparatus (e.g., light source of measuring part, light receiving element, various detecting sensors, constant-voltage (constant-current) power supply for impedance method (electric resistance method), other measurement devices, motor of sampling nozzle driving part, various pumps (including liquid supplying source, air supplying source, sucking source and syringe), display device, indicate lamp and the like.

When electric power supply to various pumps is stopped, air pressure and the pressure of various liquids may drop. The operation of a part driven only by a working fluid such as air and the like may be stopped when the supply of the working fluid such as air and the like is stopped. As for the sleep state itself, the sleep state of a conventionally-known analysis apparatus may be referred to.

The above-mentioned sleep-planned part (I) is selected from the aforementioned parts to be in a sleep state and, for example, display device, indication lamp and the like can be mentioned.

The above-mentioned part to be in a sleep state may be a total of the above-mentioned sleep-planned part (I) and the above-mentioned predetermined part (I).

Which part of the apparatus is the sleep-planned part (I) and which part of the predetermined part (I) that performs the preparatory action is placed in a sleep state after the preparatory action can be appropriately set in consideration of the energy saving performance and resource saving performance, and the user can perform the setting. The sleep-planned part (I) does not enter the sleep state until the predetermined part (I) completes the preparatory action, and when the preparatory action of the predetermined part (I) preparatory action is completed, all the parts to be put into the sleep state may be put into the sleep state simultaneously.

As for the constitution of the power supply for stopping the supply of electric power to each section by controlling the electric power supply by the control part, control technique of the power supply, and the control technique itself that the control part returns from the sleep state and starts up, the control techniques for sleep and return (resumption of operation) adopted in conventionally-known analysis apparatuses may be referred to.

(Reception of Sleep Command by Manual Input)

Figure 2:
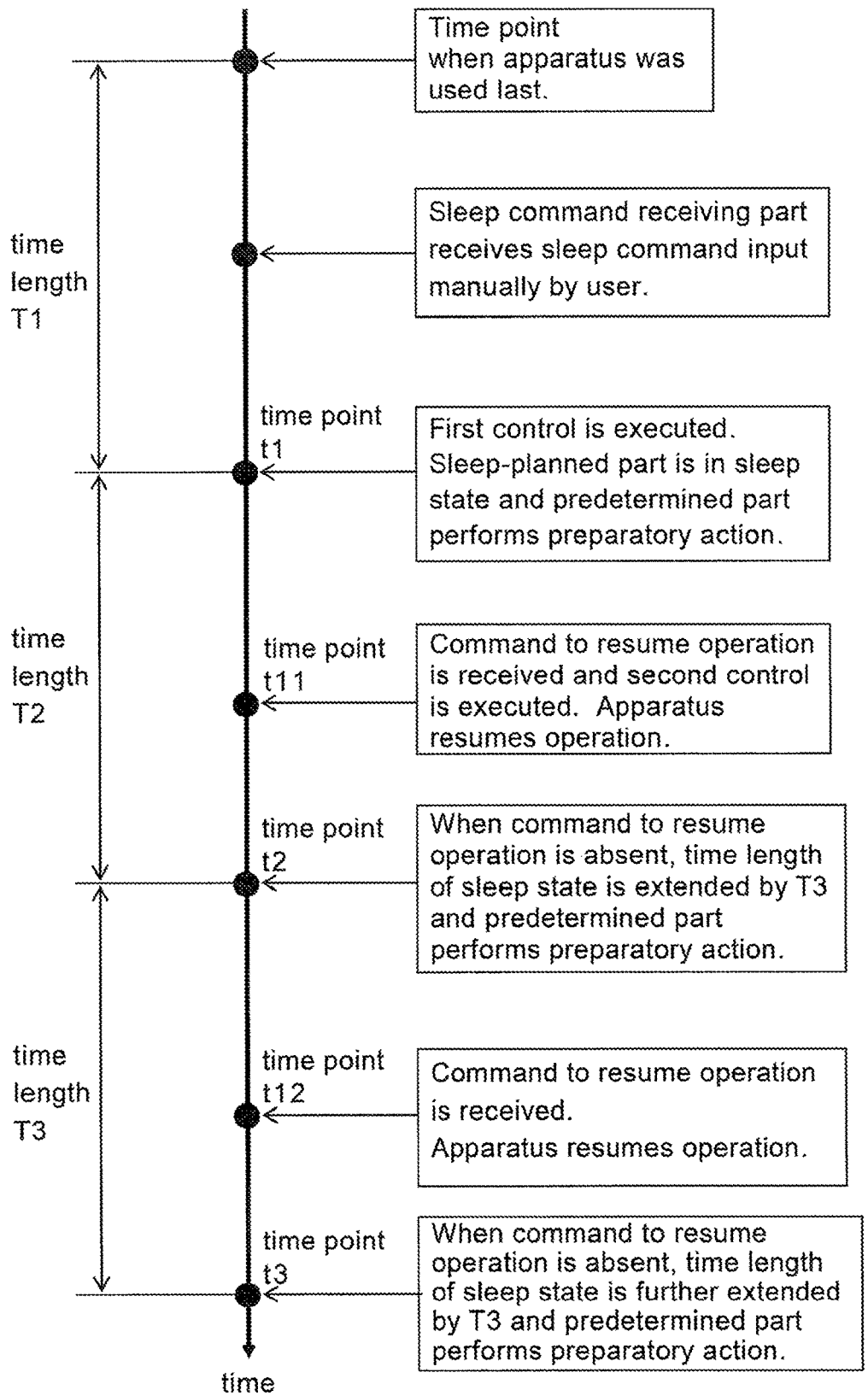
FIG. 2 is a time chart showing the time point when each control is performed when the first control and the second control are set to be performed in the present invention, and is a flowchart showing action at each time point.
Figure 3:
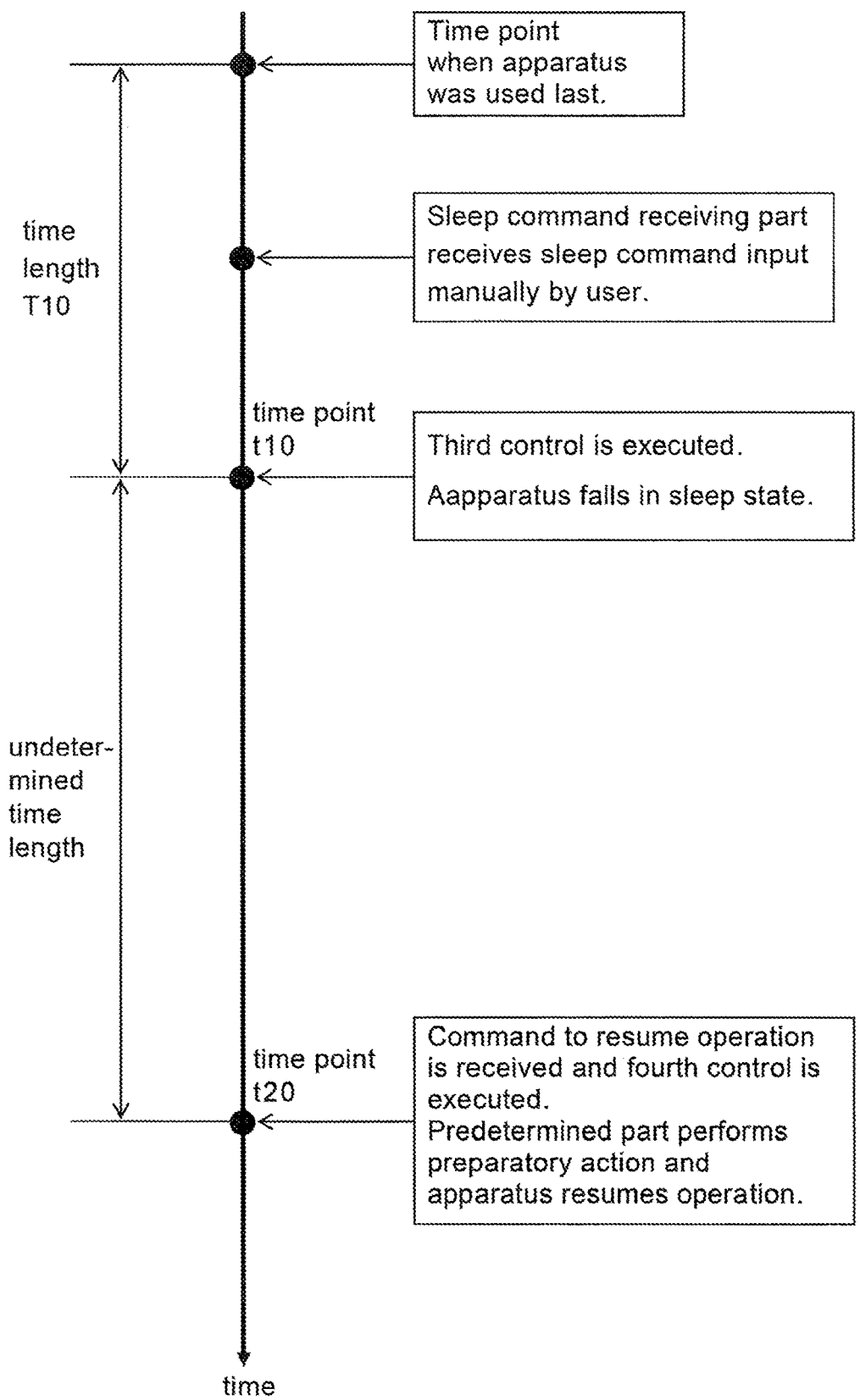
FIG. 3 is a time chart showing the time point when the third control and the fourth control are performed when the first control and the second control are set to be not performed in the present invention, and is a flowchart showing action at each time point.

As exemplified in the time charts of FIG. 2 and FIG. 3, the control part may have a sleep command receiving part for receiving a sleep command (command to put a predetermined part for the apparatus into a sleep state) manually input by the user.

The sleep command by the user in this case may be a command to set the sleep-planned part (I) to the sleep state and to cause the predetermined part to perform the preparatory action, similar to the first control, or a command to set the below-mentioned sleep-planned part (II) described later in a sleep state, similar to the third control.

The sleep command received by the sleep command receiving part may be accepted effectively and executed immediately, despite the setting of the preparatory action setting part whether it is preparatory action setting ON or preparatory action setting OFF. The timing of the receipt of the sleep command is, for example, before the first control automatically performed by the control part when the preparatory action setting is ON and before the third control automatically performed by the control part when the preparatory action setting is OFF.

The sleep command receiving part is constituted to permit the user to input the command, and receives the command input. In addition, the sleep command receiving part may be constituted such that the user can select which part is in a sleep state and which part performs a preparatory action, or the user cannot make selection and only the input of a command to set a predetermined sleep state is received.

(Preparatory Action)

The predetermined part (I) that performs a preparatory action in the first control may be determined as appropriate according to the constitution of the measuring part. Examples of the preparatory action performed in the blood analysis apparatus include blank measurement, filling of a buffer tank (dilution liquid reservoir tank) with a dilution liquid, wetting of a sampling nozzle with a dilution liquid and the like and the like. Thus, examples of the predetermined part (I) include a measuring chamber in which to perform blank measurement, buffer tank, sampling nozzle and the like.

The blank measurement is an operation including making a measurement action only with a liquid such as dilution liquid and the like without dispensing a specimen in the measuring chamber, and comparing the detection signals and the analysis results obtained by processing the detection signals with the target value for the predetermined blank measurement by the control part, thereby confirming the presence or absence of abnormality in the apparatus.

The measuring chamber in which the blank measurement is performed is not particularly limited, and may be any measuring chamber provided on the apparatus. For example, a measuring chamber (BASO chamber) 21 for counting basophils, a measuring chamber 22 for classifying and counting lymphocytes, monocytes, neutrophils, eosinophils (to be called LMNE chamber using the capital letters of Lymphocyte, Monocyte, Neutrophil, Eosinophil), a measuring chamber (RBC chamber) 23 for counting erythrocytes, and a measuring chamber (WBC chamber) 24 for count white blood cells and analyzing HGB (hemoglobin concentration) shown in FIG. 1 can be mentioned. When a measuring chamber for immunoassay such as measurement of CRP value and the like is provided in addition to these measuring chambers, blank measurement may also be performed in the measuring chamber for the immunoassay. A preparatory action unique to the present invention is described below.

[The Second Control]

The second control resumes, as exemplified in the time chart of FIG. 2, the second control of the operation of the analysis apparatus when the control part receives a command signal to resume the operation after the first control. In the example of the time chart of FIG. 2, the control part receives a command signal of operation resumption at a time point t11 between the time point t1 for performing the first control and the end-point t2 of the predetermined time length T2. A time lag may be present between the time point when the control part command receives a signal of operation resumption and the time point when the control part issues a control signal for resuming the operation of the analysis apparatus. The aforementioned preparatory action is performed in the past within the time length T2 by the first control, and therefore, the preparatory action can be omitted when the operation is resumed by the second control, and the operation can be resumed within a shorter time.

The starting point of the time length T2 may be time point t1, or a time point when a command for a preparatory action after the time point t1 is issued, or a time point when the preparatory action is completed.

(Command Signal of Operation Resumption)

A command signal for resuming operation of the apparatus may be an input signal by pressing the measurement start button by the user, a measurement start command signal sent to the apparatus through the communication line, or a detection signal sent from a sensor for detecting whether or not the user has set a specimen container to the control part or the like.

(Time Length T2)

The predetermined time length T2 is not particularly limited, and may be same value as the above-mentioned time length T1. When a biological specimen such as blood and the like is an analysis target, the time length T2 is preferably about 90 min-120 min, particularly preferable 120 min, for the same reason as in the above-mentioned time length T1.

The control part may have the recommended time length T2 as an initial set value. The control part may have a T2 setting part allowing the user to set a desired time length T2.

(Control at Time Point on Both Ends of Time Length T2)

Whether the period "between the time point t1 and the end-point t2 of the predetermined time length T2" includes time points t1, t2 at the both ends can be determined as appropriate.

For example, when the time point t1 (the first control is carried out, and at the time point of putting the sleep-planned part (I) in the sleep state) and the time point t11 when a command signal for resuming operation of the apparatus is received (time point of performing the second control) are the same, the operation may be resumed after performing the first control (i.e., after putting the sleep-planned part (I) in the sleep state and performing the preparatory action of the predetermined part (I)), or only the second control may be executed without the first control (without sleep state of sleep-planned part (I) or preparatory action of predetermined part (I)) and the operation of the apparatus may be resumed without the preparatory action.

When the end-point t2 of the time length T2 and the time point t11 when a command signal for resuming operation of the apparatus is received are the same, the second control may be executed and the operation of the apparatus may be resumed without a preparatory action, or the operation may be resumed after performing a further preparatory action.

(Control when Command Signal for Resuming Operation is not Received During the Period of Time Point t1 to t2)

When the control part does not receive a command signal for resuming operation during the period of the aforementioned time point t1 to the end-point t2 of the predetermined time length T2 (the above-mentioned time lag ΔT when absence of command signal for resuming operation is determined may be further contained after end-point t2), as shown in the time chart of FIG. 2, it is preferable that the control part further performs the preparatory action for the predetermined part (I) to further extend the sleep state of the sleep-planned part (I) by the predetermined time length T3 (the part after completion of the preparatory action may be in the sleep state). In this case, the time point t12 is the time point when the command signal for resuming operation is accepted for the first time since the last use of the apparatus.

While the time length T3 is not particularly limited, it may be the same value as the above-mentioned time length T2.

When the command signal for resuming operation is not received during the extended time length T3, a control comprising performing a further preparatory action, extending the sleep state of the sleep-planned part (I) for a time length T3 (the part with completed preparatory action is in a sleep state), whereby an action consisting of a preparatory action and extension of the time length T3 as one set is repeated until a command signal for resuming operation is received is preferable.

Whether to perform a preparatory action at the end-point t3 of the time length T3 to be extended by the required number of times can be appropriately determined similarly to the explanation of the above-mentioned whether the period "between the time point t1 and the end-point t2 of the predetermined time length T2" includes time points t1, t2 at the both ends. For example, when a command signal for resuming operation is received at the end-point t3 of the extended time length T3, the operation of the apparatus may be resumed without a preparatory action, or the operation may be resumed after a further preparatory action.

[The Third Control, the Fourth Control]

When the control part sets the above-mentioned preparatory action setting OFF by the preparation operation setting part, the control part performs the third control and the fourth control. In the third control and the fourth control, for example, switching to the sleep state and resuming operation are performed similarly to the conventional control.

In the third control, as shown in the time chart of FIG. 3, the sleep-planned part for the third control of the apparatus (hereinafter also referred to as sleep-planned part (II)) is put in a sleep state at the time point t10 when the state in which the apparatus is not used continues for the predetermined time length T10. The above-mentioned time length T10 is not particularly limited, and may be the same time length as the above-mentioned T1. When the control part receives a command signal for resuming operation at the time point t10, the control part does not put the apparatus in a sleep state and may resume the operation. In this case, the aforementioned preparatory action may or may not be performed.

While the sleep-planned part (II) is not particularly limited, for example, it may be a part including the above-mentioned sleep-planned part (I) and the above-mentioned predetermined part (I), or the whole part mentioned above to be placed in the sleep state.

In the fourth control, for example, as exemplified in the time chart of FIG. 3, at a time point t20 when a command signal for resuming operation is first received after the third control is executed (after time point t10) and undetermined time passes for the convenience of the user, a preparatory action of a predetermined part for the fourth control (hereinafter also referred to as predetermined part (II)) is performed to resume operation of the analysis apparatus. In the fourth control, the sleep state of the sleep-planned part (II) is maintained until a command signal for resuming operation is received.

The predetermined part (II) may be the same part as the above-mentioned predetermined part (I).

Preferable Embodiment 1 of the Present Invention: Recovery of Lubricating Property of Sampling Nozzle Driving Part A preferable example of the constitution of the sampling nozzle driving part is explained first.

As exemplified in FIG. 1, in the embodiments of the present invention, the sampling nozzle driving part 10 comprises a sampling nozzle (hereinafter also referred to as "nozzle") 11, a cleaning device (also referred to as sampling nozzle cleaning device) 14, and a driving unit 12 that moves them. The driving unit 12 is provided with a horizontal movement mechanism 12a and a vertical movement mechanism 12b. In the embodiments of FIG. 1, the horizontal movement mechanism 12a and the vertical movement mechanism 12b are movement mechanisms having a toothed pulley and a toothed endless belt. The nozzle 11 moves in the horizontal direction and the vertical direction by the driving unit. The cleaning device 14 is constituted to wash off dirt by running a liquid such as water, dedicated dilution liquid and the like on the outer surface of the nozzle, fixed on the horizontal movement mechanism 12a by bracket 13, and moves only in the horizontal direction. By these constitutions, the nozzle 11 can move in the vertical direction with respect to the cleaning device 14 while moving in the horizontal direction together with the cleaning device 14. These actions are attributable to the control by the control part.

Figure 4A:
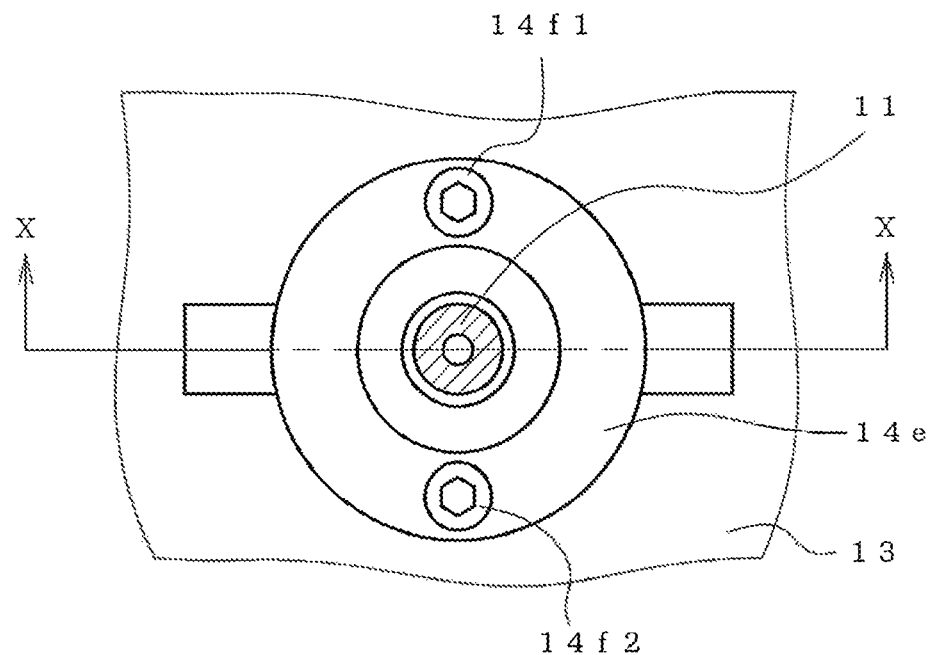
FIGS. 4(a) and 4(b) show examples of the constitution of a sampling nozzle and a cleaning device of a preferable embodiment of the present invention.
Figure 4B:
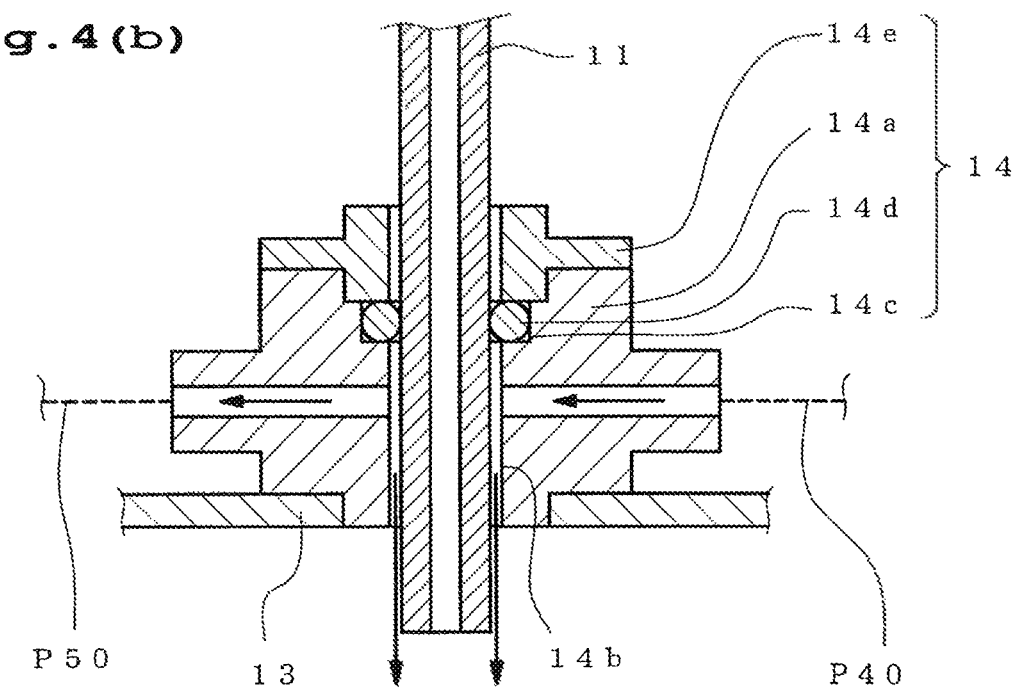

FIGS. 4(a) and 4(b) show the constitution of the nozzle and the cleaning device in FIG. 1 in detail wherein FIG. 4(a) is a top view and FIG. 4(b) is an X-X cross sectional view of FIG. 4(a). As shown in FIG. 4(b), the nozzle 11 moves in the vertical direction with respect to the cleaning device 14 while being inserted through through-hole 14b provided in the vertical direction in the main body 14a of the cleaning device 14. A piping P40 for supplying a liquid for cleaning (dilution liquid in this embodiment) into the through-hole is connected to the lower part of the main body 14a. The piping P40 is shown with a dashed line. By this constitution, the dilution liquid (arrow in the Figure) supplied by the piping P40 enters the through-hole, flows downward, falls down along the outer surface of the nozzle, and cleans the outer surface. In the embodiment of FIGS. 4(a) and 4(b), a piping P50 for discharging the air in the through-hole is also connected to the sucking source. The piping P50 is shown with a dashed line.

An O-ring groove 14c is provided in the through-hole 14b, an O-ring 14d is set in the O-ring groove 14c and the nozzle 11 passes through a circular hole in the center of the O-ring 14d. The O-ring groove 14c is closed by a lid member 14e. As shown in FIG. 4(a), the lid member 14e is fixed with bolts 14/1, 14/2 to bracket 13 together with the main body 14a. In the embodiment of FIGS. 4(a) and 4(b), the bolts 14/1, 14/2 are hexagon socket head cap bolts, and FIG. 4(a) shows the end surface of the bolt head having a hexagon socket. While not shown in FIGS. 4(a) and 4(b), lid member 14e and main body 14a are each provided with a pair of bolt holes through which bolts 14/1, 14/2 pass, and bracket 13 is provided with a pair of female screws. The lid member 14e is mounted on the main body 14a by tightening bolts 14/1, 14/2 passing through each bolt hole to the female screw of the bracket 13, and lid member 14e and main body 14a are co-fastened to the bracket 13 with the bolts 14/1, 14/2. The O-ring 14d is in contact with the outer surface of the body of the nozzle 11 while appropriately tightening the outer surface of the body, thus sealing the clearance between the nozzle 14d and the through-hole 14b while allowing the nozzle 14d to move in the vertical direction. The liquid (dilution liquid) does not rise in the clearance by the sealing with the O-ring.

In the present invention, in the preparatory action in the aforementioned first control and the fourth control, the cleaning device 14 supplies a liquid (dilution liquid) on the outer surface of the nozzle 11 as well as the nozzle reciprocates in the vertical direction by the driving unit, whereby the aforementioned liquid is supplied as a lubricating liquid to the contact interface between the aforementioned O-ring and the nozzle. In particular, the first movement of the nozzle immediately after supply of the liquid (dilution liquid) on the outer surface of the nozzle is preferably an upward movement, whereby the liquid supplied to the outer surface of the nozzle is more preferably supplied to the contact interface between the O-ring and the nozzle compared to that when the first movement of the nozzle is a downward movement. From this aspect, the position of the nozzle in a sleep state is preferably a position which can be raised by at least a predetermined distance (distance that moves the liquid supplied to the outer surface of the nozzle to the contact interface between the O-ring and the nozzle) in the preparatory action.

The aforementioned preparatory action on the nozzle affords a smooth movement of the nozzle in the vertical direction when the operation is resumed. When this preparatory action is absent, the O-ring may closely adhere to the nozzle during the unused time, and the vertical movement of the nozzle at the time of resuming operation may not be smooth. This preparatory action is preferably performed both when preparatory action setting ON and preparatory action setting OFF. Its usefulness becomes high for preparatory action setting OFF that may be left for a long time.

Preferable Embodiment 2 of the Present Invention: Difference in Preparatory Action Between Preparatory Action Setting ON and Preparatory Action Setting OFF In the present invention, the following difference in the preparatory action is recommended between preparatory action setting ON and preparatory action setting OFF.

(Difference in Blank Measurement)

In this embodiment, when set to preparatory action setting ON, the control part performs blank measurement without injecting and discharging a liquid into and from the predetermined measuring chamber. When set to preparatory action setting OFF, blank measurement is performed after injecting and discharging a liquid into and from the predetermined measuring chamber.

The aforementioned difference is formed for the following reason. With preparatory action setting ON, the blank measurement is always performed when the time length T1 or T2 passes for 120 min and the like. Thus, the measuring chamber is not left standing for an excessively long time. Accordingly, the possibility that the inner surface of the measuring chamber where the blank measurement is performed is dried is low. With preparatory action setting OFF, an automatic preparatory action is not performed for a long time far exceeding 120 min in the present invention, and the measuring chamber is left standing. Accordingly, the possibility that the inner surface of the measuring chamber where the blank measurement is performed is dried is high. When the inner surface of the measuring chamber where the blank measurement is performed is dried, crystals are developed on the inner surface and dropped crystals may cause problems such as clogging of the fine flow path of the measuring part.

Accordingly, with preparatory action setting OFF, the present invention recommends first injecting and discharging a liquid into and from the measuring chamber during blank measurement for preparatory action, thereby suppressing clogging of the fine flow path of the measuring part.

Preferable Embodiment 3 of the Present Invention: Recording Measured Value in Blank Measurement The present invention recommends recording the results of blank measurement in the preparatory action in a storage device and the like in the control part. In the embodiment of FIG. 1, the control part 200 stores in an internal storage device 240 the data of the results (analysis results) processed in the data processing part 230 that processes the detected signals. By recording the results of the blank measurement in the control part, it is possible to advantageously know from which time point the apparatus indicated abnormality.

[Constitution of Details of Measuring Part]

In the embodiment of FIG. 1, the measuring chamber 20 is constituted to be able to perform analysis methods such as impedance method, flow cytometry (optical particle analysis method), light-focused flow impedance method (impedance method and flow cytometry performed in one flow path) and the like according to the analysis object (blood cell counting, white blood cell classification, immunoassay and the like). The nozzle 11 moves in the horizontal direction and the vertical direction by the operation of the driving unit 12, the lower end side of the nozzle enters the specimen container 25 and each measuring chamber 20, and sucks or discharges the liquid. The measuring chamber 20 under control of the control part 30 performs a measurement action for analysis and sends the detection signals to the control part 30. The control part 30 processes the sent detection signals, analyzes frequency distribution and the like, and outputs the analysis results. As for the structure of each part of the measuring part 100, action for measurement (action of nozzle, action for measurement in each measuring chamber, action of various pumps and electromagnetic valve devices), and calculation processing for analysis in the control part 200, the techniques of conventionally-known analysis apparatuses of patent document 1 and the like can be referred to.

In the blood analysis apparatus shown in FIG. 1, the nozzle 11 sucks a given amount of a specimen (blood) contained in a specimen container and dispenses same in a measuring chamber 20. In the embodiment of FIG. 1, BASO chamber 21, LMNE chamber 22, RBC chamber 23, WBC chamber 24 are provided as the measuring chamber 20. A flow cell (not shown) is connected to the LMNE chamber, and the apparatus is constituted to perform processing necessary for the reagent, perform the light-focused flow impedance method in a flow cell, and count lymphocytes, monocytes, neutrophils and eosinophils. As shown in patent document 1, in addition to these measuring chambers, a measurement chamber for immunoassay such as CRP value measurement, and the like, a cleaning chamber for cleaning blood adhering to the nozzle and for dumping excess blood specimen in the nozzle may be provided. The cleaning chamber may also function as a measuring chamber.

In each measuring chamber after dispensing of the specimens, measurement data specific to the measuring chamber are obtained under control of the control part. In the control part, each measurement data sent from each measuring chamber is processed. For example, white blood cell count, red blood cell count, hemoglobin concentration, hematocrit value, average red blood cell volume, mean corpuscular hemoglobin, mean corpuscular hemoglobin concentration, platelet count, red blood cell distribution width, mean platelet volume, platelet distribution width, platelet crit, lymphocyte count, lymphocyte ratio, monocyte count, monocyte ratio, granulocyte count, granulocyte ratio, neutrophil count, neutrophil ratio, eosinophil count, eosinophil ratio, basophil count, basophil ratio, CRP value (C-reactive protein concentration), blood glucose level, and the like are analyzed in blood analysis.

The specimen may be blood, urine, feces, cell or the like, a measuring chamber according to the specimen to be analyzed can be provided, and the control part may be constituted according to the analysis of the specimen.

INDUSTRIAL APPLICABILITY

According to the present invention, an analysis apparatus having a function to enter a sleep state and capable of resuming operation more rapidly from the sleep state can be provided. In addition, the user can select whether to put the apparatus in a sleep state that can resume operation quickly or in a sleep state that can save energy and materials more. Thus, a sleep state meeting the needs of the user can be provided.

This application is based on a patent application No. 2017-138408 filed in Japan (filing date: Jul. 14, 2017), the contents of which are incorporated in full herein.

The invention claimed is:

1. An analysis apparatus comprising a measuring part for performing measurement for analysis of a specimen, and a control part for controlling the measuring part and analyzing a detection signal from the measuring part, wherein
    the control part is configured to operate in a first mode in which the control part performs a first control and a second control and operate in a second mode in which the control part performs a third control and a fourth control,
    the control part is configured to receive a setting of a user as to whether the control part operates in the first mode or in the second mode, and is configured to perform the first and second controls, or the third and fourth controls according to the setting received,
    in the first control, the control part is configured to set a sleep-planned component for the first control of the analysis apparatus to a sleep state at a time point t1 when a state of non-use of the analysis apparatus has lasted for a predetermined time length T1, and causes, at or after the time point t1, performance of preparatory actions by predetermined parts of the analysis apparatus for the first control requiring the preparatory actions to resume an analysis operation of the specimen while the sleep-planned component for the first control is still in the sleep state,
    in the second control, the control part is configured to resume the analysis operation when the control part receives a command signal to resume the analysis operation after the first control, and the preparatory actions are omitted and the analysis operation is resumed when the control part receives the command signal to resume the analysis operation after the sleep state,
    in the third control, the control part is configured to place a sleep-planned component for the third control of the analysis apparatus in a sleep state at a time point t10 when the state of non-use of the analysis apparatus has lasted for a predetermined time length T10,
    in the fourth control, the control part is configured to cause, when a command signal to resume the analysis operation is received after the third control, the preparatory actions of the predetermined parts of the analysis apparatus for the fourth control requiring the preparatory actions to resume the analysis operation, and then resume the analysis operation,
    the predetermined parts of the analysis apparatus include a measuring chamber and a sampling nozzle,
    the preparatory actions include a blank measurement performed by the measuring chamber and supplying a dilution liquid to the sampling nozzle,
    in a case where the control part is configured to execute the first control and the second control, the blank measurement is performed in the preparatory actions without injecting or discharging the dilution liquid into or from the measuring chamber, and
    in a case where the control part is configured to not execute the first control and the second control, the blank measurement is performed after injecting and discharging the dilution liquid into and from the measuring chamber in the preparatory actions.

2. The analysis apparatus according to claim 1, wherein the control part stores results of data analysis of the blank measurement.

3. The analysis apparatus according to claim 1, wherein
    the measuring part comprises a sampling nozzle driving part comprising the sampling nozzle, a cleaning device and a driving unit for moving the sampling nozzle and the cleaning device,
    the sampling nozzle is configured to move in a horizontal direction together with the cleaning device while being inserted in a through-hole provided in a vertical direction in the cleaning device, and move in the vertical direction relative to the cleaning device,
    the cleaning device comprises a liquid supply port on a lower side part of the through-hole for supplying the dilution liquid on an outer surface of the sampling nozzle, an O-ring groove is provided on an inner wall surface of the through-hole, an O-ring is set in the O-ring groove, and the O-ring seals a clearance between the through-hole and the sampling nozzle while allowing the sampling nozzle to move in the vertical direction, and
    in the preparatory actions, the dilution liquid is supplied on the outer surface of the sampling nozzle by the cleaning device, the sampling nozzle reciprocates in the vertical direction by the driving unit, whereby the dilution liquid is supplied as a lubricating liquid to a contact interface between the O-ring and the sampling nozzle.

4. The analysis apparatus according to claim 1, wherein
    the predetermined parts of the analysis apparatus further include a buffer tank, and
    the preparatory actions further include filling the dilution liquid in the buffer tank.

* * * * *